(12) United States Patent
Duffy et al.

(10) Patent No.: US 10,267,746 B2
(45) Date of Patent: Apr. 23, 2019

(54) AUTOMATED PATTERN FIDELITY MEASUREMENT PLAN GENERATION

(71) Applicant: KLA-Tencor Corporation, Milpitas, CA (US)

(72) Inventors: Brian Duffy, San Jose, CA (US); Ajay Gupta, Cupertino, CA (US); Thanh Huy Ha, Milpitas, CA (US)

(73) Assignee: KLA-Tencor Corp., Milpitas, CA (US)

( * ) Notice: Subject to any disclaimer, the term of this patent is extended or adjusted under 35 U.S.C. 154(b) by 855 days.

(21) Appl. No.: 14/918,394

(22) Filed: Oct. 20, 2015

(65) Prior Publication Data

US 2016/0116420 A1 Apr. 28, 2016

Related U.S. Application Data

(60) Provisional application No. 62/066,902, filed on Oct. 22, 2014.

(51) Int. Cl.
*G01N 21/88* (2006.01)
*G01N 23/00* (2006.01)
(Continued)

(52) U.S. Cl.
CPC ..... *G01N 21/8851* (2013.01); *G01N 21/9501* (2013.01); *G01N 23/00* (2013.01);
(Continued)

(58) Field of Classification Search
None
See application file for complete search history.

(56) References Cited

U.S. PATENT DOCUMENTS

| 6,507,029 B1 * | 1/2003 | Nishimura | B82Y 15/00 |
| | | | 250/398 |
| 6,774,990 B2 * | 8/2004 | Liang | G01N 21/6489 |
| | | | 250/492.2 |

(Continued)

FOREIGN PATENT DOCUMENTS

WO 2014/081897 5/2014

OTHER PUBLICATIONS

International Search Report for PCT/US2015/056772 dated Feb. 5, 2016.

(Continued)

*Primary Examiner* — Iman K Kholdebarin
(74) *Attorney, Agent, or Firm* — Ann Marie Mewherter

(57) ABSTRACT

Methods and systems for determining parameter(s) of a metrology process to be performed on a specimen are provided. One system includes one or more computer subsystems configured for automatically generating regions of interest (ROIs) to be measured during a metrology process performed for the specimen with the measurement subsystem based on a design for the specimen. The computer subsystem(s) are also configured for automatically determining parameter(s) of measurement(s) performed in first and second subsets of the ROIs during the metrology process with the measurement subsystem based on portions of the design for the specimen located in the first and second subsets of the ROIs, respectively. The parameter(s) of the measurement(s) performed in the first subset are determined separately and independently of the parameter(s) of the measurement(s) performed in the second subset.

27 Claims, 6 Drawing Sheets

(51) Int. Cl.
  *G01N 21/95* (2006.01)
  *G03F 7/20* (2006.01)
  *G01N 21/956* (2006.01)

(52) U.S. Cl.
  CPC ....... *G03F 7/70625* (2013.01); *G01N 21/956* (2013.01); *G01N 2021/8883* (2013.01)

(56) References Cited

U.S. PATENT DOCUMENTS

| | | | |
|---|---|---|---|
| 6,886,153 B1 | 4/2005 | Bevis | |
| 6,902,855 B2 | 6/2005 | Peterson et al. | |
| 7,241,991 B1 | 7/2007 | Standiford et al. | |
| 7,418,124 B2 | 8/2008 | Peterson et al. | |
| 7,570,796 B2 | 8/2009 | Zafar et al. | |
| 7,571,422 B2 | 8/2009 | Adel et al. | |
| 7,676,077 B2 | 3/2010 | Kulkarni et al. | |
| 7,769,225 B2 | 8/2010 | Kekare et al. | |
| 7,796,801 B2* | 9/2010 | Kitamura | G06K 9/00 348/125 |
| 7,853,920 B2 | 12/2010 | Preil et al. | |
| 8,041,106 B2 | 10/2011 | Pak et al. | |
| 8,194,968 B2 | 6/2012 | Park et al. | |
| 8,213,704 B2 | 7/2012 | Peterson et al. | |
| 8,453,075 B2 | 5/2013 | Guo et al. | |
| 8,547,429 B2 | 10/2013 | Honda et al. | |
| 8,559,001 B2 | 10/2013 | Chang et al. | |
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 8,755,045 B2 | 6/2014 | Lin et al. | |
| 8,923,600 B2 | 12/2014 | Zafar et al. | |
| 9,087,367 B2 | 7/2015 | Chang et al. | |
| 2002/0054703 A1* | 5/2002 | Hiroi | G01N 21/9501 382/149 |
| 2002/0161534 A1* | 10/2002 | Adler | G01N 21/956 702/35 |
| 2002/0171051 A1* | 11/2002 | Nakagaki | G01N 21/9501 250/559.4 |
| 2003/0219153 A1* | 11/2003 | Levin | G01N 21/9501 382/141 |
| 2009/0179161 A1* | 7/2009 | Ward | B82Y 10/00 250/492.21 |
| 2009/0290782 A1* | 11/2009 | Regensburger | G05B 23/0216 382/145 |
| 2009/0297019 A1* | 12/2009 | Zafar | G03F 1/84 382/145 |
| 2011/0170091 A1 | 7/2011 | Chang et al. | |
| 2012/0029858 A1 | 2/2012 | Kulkarni et al. | |
| 2012/0216169 A1 | 8/2012 | Park et al. | |
| 2012/0243773 A1 | 9/2012 | Kulkarni et al. | |
| 2012/0257041 A1* | 10/2012 | Nakagaki | H01J 37/28 348/80 |
| 2012/0308112 A1* | 12/2012 | Hu | G01N 21/9501 382/149 |
| 2013/0176558 A1* | 7/2013 | Lin | G01B 11/24 356/237.5 |
| 2014/0105482 A1 | 4/2014 | Wu et al. | |
| 2014/0198975 A1* | 7/2014 | Nakagaki | G01N 23/2251 382/149 |
| 2014/0270474 A1 | 9/2014 | Huang et al. | |
| 2015/0012900 A1 | 1/2015 | Shifrin et al. | |
| 2015/0268177 A1* | 9/2015 | Yokochi | G01N 21/9501 356/237.5 |
| 2015/0293035 A1* | 10/2015 | Gaind | G01N 21/9501 356/237.5 |
| 2015/0332452 A1* | 11/2015 | Tsuchiya | G06T 7/0004 382/147 |
| 2016/0025618 A1* | 1/2016 | Ryu | G01N 21/211 356/369 |
| 2018/0261424 A1* | 9/2018 | Tsuchiya | H01J 37/222 |

OTHER PUBLICATIONS

Lorusso et al., "Advanced DFM applications using Design Based Metrology on CD SEM," Proc. SPIE 6152, Metrology, Inspection, and Process Control for Microlithography XX, 61520B (Mar. 27, 2006), 13 pages.

Jank et al., "Method for fast and accurate calibration of litho simulator for hot spot analysis," IEEE International Symposium on Semiconductor Manufacturing 2006, ISSM 2006, Oct. 2006, 4 pages.

* cited by examiner

AUTOMATED PATTERN FIDELITY MEASUREMENT PLAN GENERATION

BACKGROUND OF THE INVENTION

1. Field of the Invention

The present invention generally relates to automated pattern fidelity measurement plan generation. Certain embodiments relate to methods and systems for determining one or more parameters of a metrology process to be performed on a specimen.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Defect review typically involves re-detecting defects detected as such by an inspection process and generating additional information about the defects at a higher resolution using either a high magnification optical system or a scanning electron microscope (SEM). Defect review is therefore performed at discrete locations on the wafer where defects have been detected by inspection. The higher resolution data for the defects generated by defect review is more suitable for determining attributes of the defects such as profile, roughness, more accurate size information, etc. Since the defect review is performed for defects detected on the wafer by inspection, the parameters used for defect review at a location of a detected defect may be determined based on attributes of the defects determined by the inspection process. However, the output acquisition parameters (e.g., optical, electron beam. etc. parameters) used for defect review at a location of a detected defect are generally not determined based on information about the portion of the design in or near the location of the defect because such information is generally irrelevant to the output acquisition functions performed for the detected defects during defect review.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined using currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at which a metrology process is performed on a wafer may be independent of the results of an inspection process performed on the wafer. In particular, the locations at which a metrology process is performed may be selected independently of inspection results. In addition, since locations on the wafer at which metrology is performed may be selected independently of inspection results, unlike defect review in which the locations on the wafer at which defect review is to be performed cannot be determined until the inspection results for the wafer are generated and available for use, the locations at which the metrology process is performed may be determined before an inspection process has been performed on the wafer.

Current methods used for setting up metrology processes have a number of disadvantages. For example, conventional recipe setup for pattern metrology (including, for example, critical dimension (CD) and overlay measurements) with a SEM requires prior knowledge of the locations that are to be measured. In addition, the conventional recipe setup process often includes the use of the design. Furthermore, if a new pattern of interest (POI) is discovered that the user wants to measure once or on an ongoing basis, it requires an update of the metrology tool recipe.

Accordingly, it would be advantageous to develop systems and methods for determining one or more parameters of a metrology process to be performed on a specimen that do not have one or more of the disadvantages described above.

SUMMARY OF THE INVENTION

The following description of various embodiments is not to be construed in any way as limiting the subject matter of the appended claims.

One embodiment relates to a system configured to determine one or more parameters of a metrology process to be performed on a specimen. The system includes a measurement subsystem including at least an energy source and a detector. The energy source is configured to generate energy that is directed to a specimen. The detector is configured to detect energy from the specimen and to generate output responsive to the detected energy. The system also includes one or more computer subsystems configured for automatically generating regions of interest (ROIs) to be measured during a metrology process performed for the specimen with the measurement subsystem based on a design for the specimen. The one or more computer subsystems are also configured for automatically determining one or more parameters of one or more measurements performed in first and second subsets of the ROIs during the metrology process with the measurement subsystem based on portions of the design for the specimen located in the first and second subsets of the ROIs, respectively. The one or more parameters of the one or more measurements performed in the first subset are determined separately and independently of the one or more parameters of the one or more measurements performed in the second subset. The system may be further configured as described herein.

Another embodiment relates to a computer-implemented method for determining one or more parameters of a metrology process to be performed on a specimen. The method includes the automatically generating and automatically determining steps described above. The steps of the method are performed by one or more computer systems.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for determining one or more parameters of a metrology process to be performed on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
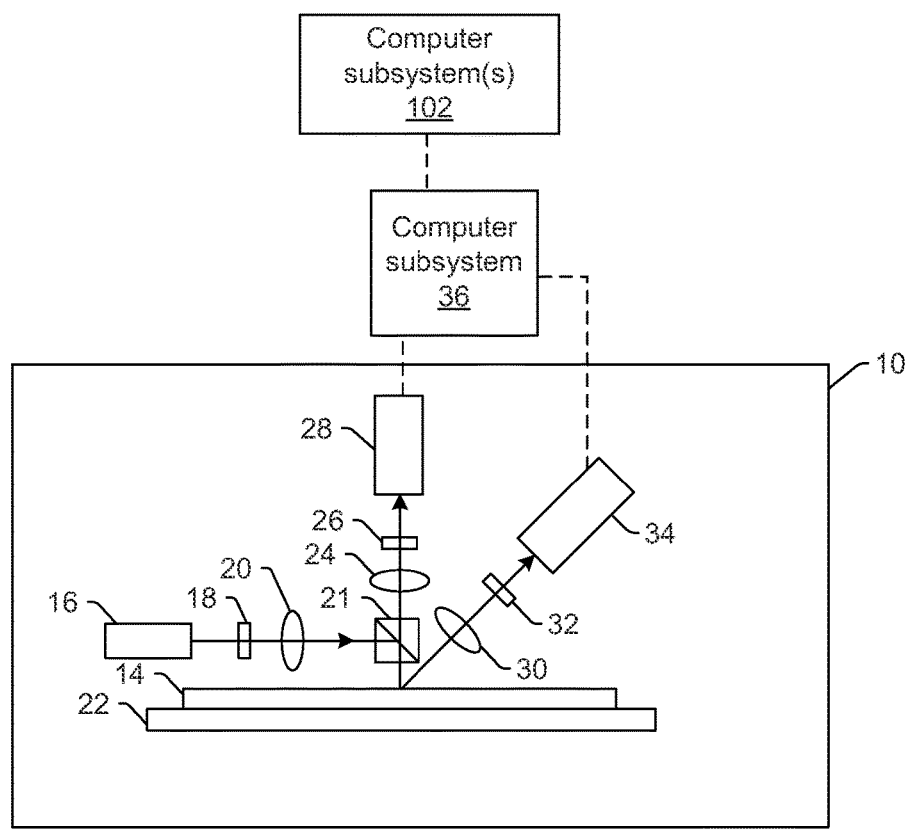
FIGS. 1 and 2 are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. The physical design may be stored in a data structure such as a graphical data stream (GDS) file, any other standard machine-readable file, any other suitable file known in the art, and a design database. A GDSII file is one of a class of files used for the representation of design layout data. Other examples of such files include GL 1 and OASIS files and proprietary file formats such as RDF data, which is proprietary to KLA-Tencor, Milpitas, Calif. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In some instances, simulated or acquired images from a wafer or reticle can be used as a proxy for the design. Image analysis can also be used as a proxy for design analysis. For example, polygons in the design may be extracted from an image of a design printed on a wafer and/or reticle, assuming that the image of the wafer and/or reticle is acquired with sufficient resolution to adequately image the polygons of the design. In addition, the "design" and "design data" described herein refers to information and data that is generated by semiconductor device designers in a design process and is therefore available for use in the embodiments described herein well in advance of printing of the design on any physical wafers.

Preferably, the "design" or "physical design" as those terms are used herein refer to the design as it would be ideally formed on the wafer. In this manner, a design or physical design described herein would preferably not include features of the design that would not be printed on the wafer such as optical proximity correction (OPC) features, which are added to the design to enhance printing of the features on the wafer without actually being printed themselves. In this manner, in some embodiments, the design for the specimen used for the automatically generating and the automatically determining steps described further herein does not include features of the design that will not be printed on the specimen.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to determine one or more parameters of a metrology process to be performed on a specimen. In one embodiment, the specimen includes a wafer. In another embodiment, the specimen includes a reticle. The wafer and the reticle may include any wafer and reticle known in the art.

One embodiment of such a system is shown in FIG. 1. The system includes a measurement subsystem that includes at least an energy source and a detector. The energy source is configured to generate energy that is directed to a specimen. The detector is configured to detect energy from the specimen and to generate output responsive to the detected energy.

In one embodiment, the energy directed to the specimen includes light, and the energy detected from the specimen includes light. For example, in the embodiment of the system shown in FIG. 1, measurement subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the measurement subsystem may be configured to alter one or more characteristics of one or more elements of the illumination subsystem such that the light can be directed to the specimen at an angle of incidence that is different than that shown in FIG. 1. In one such example, the measurement subsystem may be configured to move light source 16, optical element 18, and lens 20 such that the light is directed to the specimen at a different angle of incidence.

In some instances, the measurement subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by changing the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for metrology.

The measurement subsystem may also include a scanning subsystem configured to cause the light to be scanned over the specimen. For example, the measurement subsystem may include stage 22 on which specimen 14 is disposed during measurement. The scanning subsystem may include any suitable mechanical and/or robotic assembly (that includes stage 22) that can be configured to move the specimen such that the light can be scanned over the specimen. In addition, or alternatively, the measurement subsystem may be configured such that one or more optical elements of the measurement subsystem perform some scanning of the light over the specimen. The light may be scanned over the specimen in any suitable fashion.

The measurement subsystem further includes one or more detection channels. At least one of the one or more detection channels includes a detector configured to detect light from the specimen due to illumination of the specimen by the measurement subsystem and to generate output responsive to the detected light. For example, the measurement subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the measurement subsystem that includes two detection channels, the measurement subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the measurement system may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the images described herein in a number of ways.

It is noted that FIG. 1 is provided herein to generally illustrate a configuration of a measurement subsystem that may be included in the system embodiments described herein. Obviously, the measurement subsystem configuration described herein may be altered to optimize the performance of the system as is normally performed when designing a commercial metrology system. In addition, the systems described herein may be implemented using an existing metrology system (e.g., by adding functionality described herein to an existing metrology system) such as the SpectraShape family of tools and the Archer series of tools that are commercially available from KLA-Tencor. For some such systems, the methods described herein may be provided as optional functionality of the metrology system (e.g., in addition to other functionality of the metrology system). Alternatively, the metrology system described herein may be designed "from scratch" to provide a completely new metrology system.

Computer subsystem 36 of the system may be coupled to the detectors of the measurement subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number functions using the output of the detectors as described herein and any other functions described further herein. This computer subsystem may be further configured as described herein.

This computer subsystem (as well as other computer subsystems described to herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the measurement subsystem is described above as being an optical or light-based measurement subsystem, the measurement subsystem may be an electron beam-based measurement subsystem. For example, in one embodiment, the energy directed to the specimen includes electrons, and the energy detected from the specimen includes electrons. In this manner, the energy source may be an electron beam source. In one such embodiment shown in FIG. 2, the measurement subsystem includes electron column 122, which is coupled to computer subsystem 124.

Figure 2:
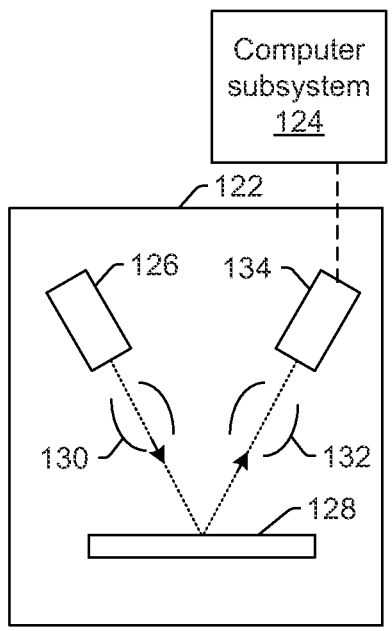

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No.

8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based measurement subsystem may be configured to use multiple modes to generate images of the specimen (e.g., with different illumination angles, collection angles, etc.). The multiple modes of the electron beam-based measurement subsystem may be different in any image generation parameters of the measurement subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the measurement subsystem shown in FIG. 2 may be further configured as described herein.

It is noted that FIG. 2 is provided herein to generally illustrate a configuration of an electron beam-based measurement subsystem that may be included in the embodiments described herein. As with the optical measurement subsystem described above, the electron beam-based measurement subsystem configuration described herein may be altered to optimize the performance of the measurement subsystem as is normally performed when designing a commercial metrology system. In addition, the systems described herein may be implemented using an existing metrology or high resolution defect review system (e.g., by adding functionality described herein to an existing metrology system) such as the eDR-xxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the measurement subsystem is described above as being a light-based or electron beam-based measurement subsystem, the measurement subsystem may be an ion beam-based measurement subsystem. Such a measurement subsystem may be configured as shown in FIG. 2 except that the electron beam source may be replaced with any suitable ion beam source known in the art. In addition, the measurement subsystem may be any other suitable ion beam-based measurement subsystem such as those included in commercially available focused ion beam (FIB) systems, helium ion microscopy (HIM) systems, and secondary ion mass spectroscopy (SIMS) systems.

The one or more computer subsystems included in the system embodiments described herein are configured for automatically generating regions of interest (ROIs) to be measured during a metrology process performed for the specimen with the measurement subsystem based on a design for the specimen. Since the ROIs are determined based on the design for the specimen, the ROIs may be referred to as "design-based ROIs." In addition, the metrology process for which one or more parameters are determined as described herein may be referred to as a "design driven metrology process."

Figure 3:
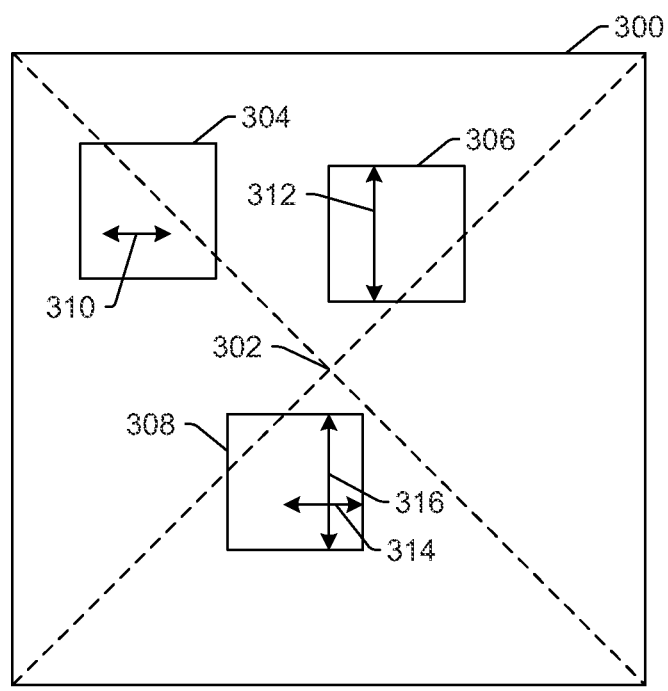
FIG. 3 is a schematic diagram illustrating a plan view of one embodiment of the relationship between various terms used herein including measurement site, field of view, and region of interest.

FIG. 3 provides some context for various terms used herein including ROI. For example, FIG. 3 shows field of view (FOV) 300 for a measurement subsystem such as one of those described herein centered on measurement site 302. The measurement site may be a site of a detected defect (detected by inspection and/or review) or a sampled site. Each FOV location on the wafer during a metrology process may be associated with only one of the measurement sites for which the metrology process will be performed. For example, during a metrology process, a scanning electron microscope (SEM) or other measurement subsystem may drive from measurement site to measurement site.

As also shown in FIG. 3, within FOV 300, there may be located multiple ROIs 304, 306, and 308. Although three ROIs are shown in FIG. 3, there may be any number of ROIs in any one FOV (i.e., one or more ROIs). As further shown in FIG. 3, the ROIs may be located in a variety of locations within the FOV, and although the three ROIs are shown as not overlapping in the FOV, the ROIs may in some instances overlap to some extent in the FOV. Within each of the ROIs, at least one measurement may be selected to be performed, which may be automatically selected or determined as described further herein. Although FIG. 3 does not shown any patterned features that would be formed in the area of the wafer located in the FOV shown in FIG. 3, the measurements will generally be for one or more characteristics of the patterned features.

To illustrate different measurements that may be performed in different ROIs, FIG. 3 illustrates these different measurements abstractly as double headed arrows showing the extent and direction of the dimension across which such measurements may be performed. For example, as shown in FIG. 3, measurement 310 may be performed in ROI 304 in one direction across only a portion of an entire dimension of the ROI in that direction. Measurement 312 may be performed in ROI 306 in a different direction across an entire dimension of the ROI in that direction. In addition, measurements 314 and 316 may be performed in perpendicular directions across ROI 308. Measurement 314 may be performed across only a portion of an entire dimension of the ROI in the direction of that measurement while measurement 316 may be performed across an entire dimension of the ROI in the direction of that measurement. Therefore, as described further herein, different measurements may be performed in different ROIs, and the measurements performed in any one ROI may be selected or determined as described further herein.

The one or more computer subsystems are also configured for automatically determining one or more parameters of one or more measurements performed in first and second subsets of the ROIs during the metrology process with the measurement subsystem based on portions of the design for the specimen located in the first and second subsets of the ROIs, respectively. The one or more parameters of the one or more measurements performed in the first subset are determined separately and independently of the one or more parameters of the one or more measurements performed in the second subset. In other words, the one or more parameters may be determined for the first subset of the ROIs based on only the portion of the design located in the first subset, the one or more parameters may be determined for the second subset of the ROIs based on only the portion of the design located in the second subset, and so on. In addition, although some embodiments are described herein with respect to first and second subsets, it is to be understood that the step(s) performed by the computer subsystem(s) may be performed for more than two subsets of the ROIs (e.g., two or more subsets of ROIs). Furthermore, each of the subsets of the ROIs may include one or more ROIs. For example, the first subset of the ROIs may include only one ROI while the second subset of the ROIs may include more than one ROI. In this manner, the embodiments described herein are configured for automated pattern fidelity measurement plan generation. The embodiments described herein may also be configured for execution of the pattern fidelity measurement plans that are generated.

In one embodiment, the automatically generating and the automatically determining are performed during setup of the metrology process. In this manner, the method may include automatic ROI generation during setup using the physical design for the wafer. In addition, recipe setup for pattern fidelity measurements may be fully automated since ROIs for thousands of unique sites can be automatically generated during setup.

In another embodiment, the automatically generating and the automatically determining are performed on-the-fly during runtime of the metrology process. In this manner, the embodiments described herein may be configured for automated on-the-fly pattern fidelity measurement plan generation. In addition, the method may include automatic ROI generation during runtime using the physical design for the wafer.

The embodiments described herein also can generate a metrology measurement plan without the need to have prior knowledge of the structures to be measured. For example, the embodiments described herein do not necessarily perform functions using information generated by another system or method for the structures to be measured. Therefore, the embodiments described herein provide a number of advantages over currently used methods and systems for measurement plan generation. For example, at new process nodes, pattern deviations detected by inspection tools will require quantitative analysis to determine whether they meet the criteria of being a "defect." One cannot anticipate in advance where these defect candidates may appear, thus the need for automated metrology plan generation on-the-fly.

In some embodiments, the automatically generating includes performing rules-based searching of the design during setup of the metrology process. For example, recipe setup for pattern fidelity measurements can be fully automated since ROIs for thousands of unique sites can be automatically generated using a rules-based search of the physical design for the wafer during setup. In this manner, the embodiments described herein may be configured for rule-based automatic ROI generation.

Applying rules for ROI generation to a design may be performed in a number of different ways. For example, a rule-based approach may be a non-image processing to approach in which rules are applied to design data to generate the ROIs. Such applying may be performed using CAD software. In another example, an image processing based approach may be used which may include rendering of the design data as an image and then using image processing algorithms to generate ROIs using rules as input. In this manner, the design data may be consumed by various types of design analysis software and/or algorithms in order to generate ROIs using rules as input.

In one embodiment of a rule-based search for automatically generating the ROIs, one rule may be created for each different measurement type. In other words, rule 1 may be for measurement type 1, rule 2 may be for measurement type 2, and so on. In addition, each rule may not be for more than one measurement type. In this manner, each rule may define the characteristics of the pattern in the design to be formed on the wafer that would make a measurement of its measurement type suitable for that pattern. For example, a rule for a line width measurement type may be designed to identify patterns or portions of patterns that have a substantially uniform dimension across a relatively large section of the patterns as candidates for line width measurement types.

In some such instances, each of the rules may be performed for any and/or all of the patterns included in any one FOV. Therefore, all of the rules may be executed on a per FOV basis. Since each rule may identify possible locations for measurements of the type for which it was written, each rule may identify a number of possible ROIs for that FOV, where each potential location for a measurement type corresponds to one of the ROIs. Therefore, the results of applying each rule to each FOV may include one or more ROI locations in the FOV. As such, applying multiple rules to each FOV may produce one or more ROI locations in each FOV, some of which may correspond to different measurement types. In some such instances, each of the ROI locations within the FOV may correspond to only one measurement of only one type. However, it is possible that multiple ROI locations within a FOV may overlap (partially or completely) with each other within the FOV (e.g., when it is appropriate to perform two different measurements of two different types in the same portion of the FOV). In such instances, of the overlapping ROIs, each individual ROI may correspond to only one measurement of only one measurement type. In other words, there may be only one measurement type per ROI. Therefore, in order to perform multiple measurements for a given ROI location, there may be multiple ROIs created, with each ROI having the same ROI bounds (or location, coordinates, etc.) but each having different measurement types.

To summarize, therefore, for any one measurement site on a wafer, one FOV may be designated for that measurement site. All rules may be run for each FOV. As a result of running all of the rules, one or more ROIs per rule per FOV may be generated with one measurement per ROI. The same steps may be repeated for each FOV/measurement site until all of the FOVs/measurement sites have been processed.

In one embodiment, the one or more computer subsystems include a computer subsystem of an electronic design automation (EDA) tool. For example, for ROI generation at runtime, the method may use EDA physical design analysis tools or apply custom algorithms to the physical design. In some such instances, a design clip or another representation of the design may be automatically analyzed by physical design analysis software to determine the valid measurements within the design clip or other representation of the design. In one such example, for ROI generation at runtime, an algorithm may automatically segment the design based on whether a given segment of the pattern is straight/parallel (i.e., the two edges of a structure/pattern are parallel to each other), curved (e.g., on a corner), or at the end of a line. The EDA tool may include any suitable commercially available EDA tool. In some such embodiments, one or more of the computer subsystems described herein (e.g., computer subsystem(s) 102) may be configured as an EDA tool.

In another embodiment, the one or more parameters automatically determined for the first subset of the ROIs result in a first type of the measurement(s) performed in the first subset of the ROIs, the one or more parameters automatically determined for the second subset of the ROIs result in a second type of the measurement(s) performed in the second subset of the ROIs, and the first and second types of the measurement(s) are different from each other. In this manner, the method may include automatic determination of measurement type during the ROI generation process. There may be one measurement type per ROI and may be automatically determined during the ROI generation process. As such, the embodiments described herein may be configured for automatic generation of metrology plans with appropriate measurement types for each ROI. For example, the metrology plan generation may include, for each FOV, automatically defining ROIs and measurement type from the physical design. Automatically defining the ROIs and the measurement type may be performed using design analysis algorithms and software. The one or more parameters may also include where in the ROI that the measurement type is to be performed. The location in the ROI where the measurement type is to be performed may be determined as described further herein.

The metrology processes described herein may be performed to determine how patterns on a wafer differ from the patterns in the design. In particular, the patterns as they are designed to be printed on a wafer are almost never printed on the wafer exactly as they are designed. Such differences in the as-designed patterns from the as-printed patterns can be due to the inherent limitations in the processes, tools, and materials used to print the patterns on the wafer as well as any errors in the processes, tools, and materials.

Figure 4:
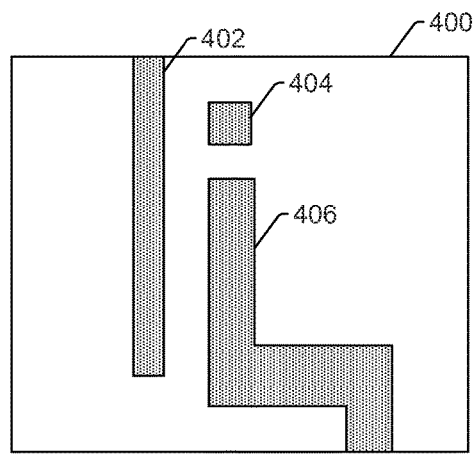
FIG. 4 is a schematic diagram illustrating a plan view of one example of a portion of a design for a wafer as the portion of the design appears in design space.
Figure 5:
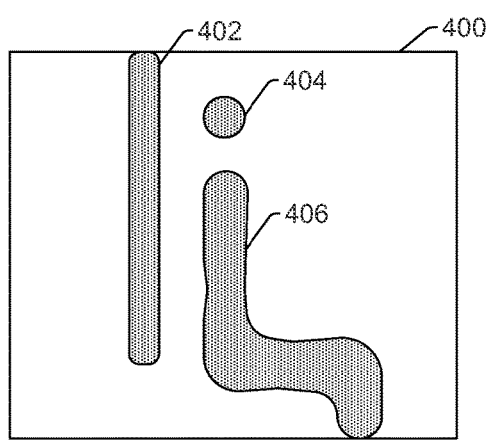
FIG. 5 is a schematic diagram illustrating a plan view of one example of the portion of the design shown in FIG. 4 as the portion of the design may be printed on a wafer.

One example of how patterns printed on a wafer can be different from patterns as-designed is shown in FIGS. 4 and 5. In particular, as shown in FIG. 4, portion 400 of a design for a wafer (not shown in FIG. 4) may include three different patterns 402, 404, and 406. Pattern 402 is an example of a line structure that may be included in a design for a wafer. Pattern 404 is an example of a contact structure that may be included in a design for a wafer, and pattern 406 is an example of a polygon structure that may be included in a design for a wafer.

Although some examples of structures that may be included in a design for a wafer are shown in FIG. 4 (and other figures described herein), the examples are not meant to be representative of any particular design for any particular wafer. Instead, as will be clear to one of ordinary skill in the art, the design for the wafer may include many different types of structures in many different arrangements and in many different numbers. The structures shown in FIG. 4 (and other figures described herein) are merely meant to illustrate some hypothetical wafer structures to further understanding of various embodiments described herein.

Due to the inherent limitations of the tools, materials, and processes used to print the structures shown in portion 400 of the design, the structures will not necessarily be printed on the wafer as they are included in the design. For example, as shown in FIG. 5, instead of patterns 402, 404, and 406 in portion 400 having sharp, 90 degree corners as shown in the design, the patterns will have at least somewhat rounded corners. In addition, any of the structures may have variations in dimensions such as width at various points across the structures. For example, as shown in FIG. 5, pattern 406 has some line width variations compared to the design characteristics of this structure at multiple points across the structure.

Figure 6:
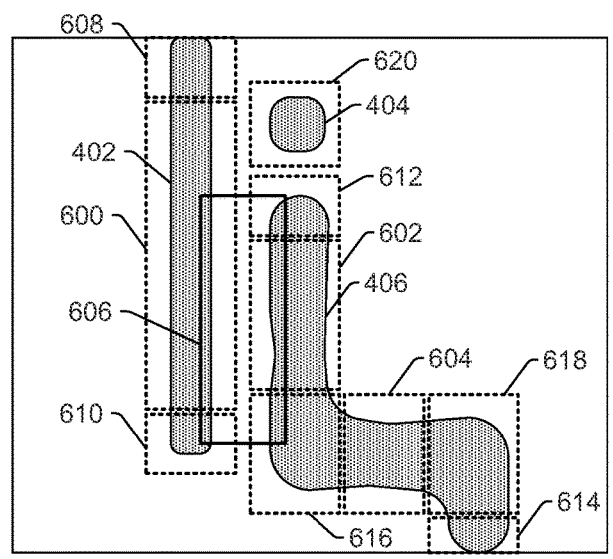
FIG. 6 is a schematic diagram illustrating a plan view of one embodiment of the portion of the design shown in FIG. 5 with different regions of interest within the portion of the design.

The ROIs and measurement type per ROI may therefore be selected automatically as described herein based on the characteristics of the as-designed patterns, possibly in combination with some a priori knowledge of the potential issues with the patterns. A number of possible ROIs are shown in FIG. 6 for the patterns shown in FIG. 5. Although these possible ROIs are shown with respect to the patterns shown in FIG. 5, the ROIs may actually be determined based on the design corresponding to the patterns shown in FIG. 5. i.e., based on the patterns as they are shown in FIG. 4.

In the embodiment shown in FIG. 6, ROIs 600, 602, and 604 may be determined for portions of the features that are designed to have substantially uniform dimensions across a portion of the features. For example, ROI 600 may be generated for a portion of feature 402 designed to have substantially uniform dimensions across that portion, and ROIs 602 and 604 may be generated for portions of feature 406 designed to have substantially uniform dimensions across those portions. The measurement type automatically selected for these ROIs may be a line width measurement, which may be used to detect necking or bulging issues in the patterned features.

Another ROI, ROI 606, may be generated automatically for a space between two of the features, features 402 and 406, that is designed to have substantially the same dimensions across the ROI. The measurement type automatically selected for this ROI by the embodiments described herein may include a gap measurement (or a distance or some statistical measure of distance between the two features). Gap measurements may be performed to detect bridging issues between two patterned features.

The embodiments described herein may also be configured to automatically generate a number of ROIs at and/or near the ends of one or more of the features. For example, as shown in FIG. 6, ROIs 608 and 610 may be automatically generated for the ends of feature 402 while ROIs 612 and 614 may be automatically generated for the ends of feature 406. The measurement type selected for these ROIs may be line end position, line end pullback, line end distance (e.g., distance between the two line ends of a straight line) or some other measurement type that can be used to describe the relative position of the end of the feature as-designed versus as-printed.

One or more ROIs may also be generated automatically for the corner of one or more of the patterned features in the design. For example, as shown in FIG. 6, ROIs 616 and 618 may be generated for corners of feature 406. The measurement type selected for these ROIs may be curvature, radius, distance, arc area, or some other measurement type that can be used to describe the shape of the corner.

Another ROI may be generated automatically by the embodiments described herein for the contact patterned feature in the design. For example, as shown in FIG. 6, ROI 620 may be generated for contact feature 404. The measurement type selected for this ROI may be diameter, width, height, radius, area, or another measurement type that can be used to describe how the contact as-printed is different from the contact as-designed.

Other measurement types that may be determined for a metrology process include tip-to-tip (a measurement of the gap between two line ends), tip-line (a measurement of the gap between a line end and a line), line length (a measurement of the length of a straight line), and corner-to-corner measurements.

As described above, therefore, the embodiments described herein may be configured to perform design-based segmentation of at least a portion of a design for a wafer into ROIs for a metrology process. In addition, some of the segments may include straight line segments, straight gap segments, line end segments, corner segments, and contact segments. The different segments and corresponding ROIs may be determined in the design in a number of different ways described herein. For example, the segments or ROIs may be determined by applying one or more rules to the design. In another example, imaginary center lines (imaginary in the sense that they are not part of the design or printed on the wafer) through patterned features in the design may be identified as described further herein and then those center lines can be used to segment the patterned features into segments and/or ROIs. For example, a straight center line through a patterned feature may be used to identify the portion of the patterned feature through which the straight center line runs as a straight line segment. In another example, a straight center line through a space between two patterned features may be used to identify the portion of the space through which that straight center line runs as a straight gap segment. In an additional example, a portion of a patterned feature in which two straight lines meet at a 90 degree angle may be identified as a corner segment. Other segments described herein can be identified in a similar manner using the imaginary center lines.

Once the various locations for the metrology process have been determined (e.g., measurement site locations, alignment site locations, auto-focus site locations, etc.), the metrology recipe setup may include various additional steps, some of which may be performed on the metrology tool using a physical wafer. For example, one or more of the locations may be positioned in a FOV of the measurement subsystem. Once the one or more locations are positioned in the FOV of the measurement subsystem, output of the measurement subsystem may be generated using different values for parameters of the measurement subsystem, i.e., optical, electron beam, or imaging parameters. Different output generated using different values of the parameters may then be compared to determine which of the parameters are best for use in the metrology process for the one or more locations. In addition, different measurement subsystem parameters may be selected for different locations that will be measured in the same metrology process. For example, one set of measurement subsystem parameters may be determined to be the best (and therefore selected) for one measurement type in one type of ROI while another, different set of measurement subsystem parameters may be determined to be the best (and therefore selected) for another, different measurement type in another, different type of ROI. In a similar manner, one or more parameters of one or more methods and/or algorithms applied by the computer subsystem(s) to the output generated by the measurement subsystem may be determined on a location type-by-location type basis (such that different methods and/or algorithms and/or different parameters of the same method(s) and/or algorithm(s) may be applied to the output generated at different types of locations on the wafer).

In some embodiments, the computer subsystem(s) are configured for determining locations on the specimen of the first and second subsets of the ROIs during the metrology process by aligning the output of the detector to the design for the specimen. For example, the computer subsystems may be configured for automatic SEM-to-design fine alignment (e.g., using geometries in the FOV of the SEM). SEM-to-design fine alignment may be performed since global alignment does not guarantee alignment of center lines of structures in images generated by a measurement subsystem and design structures.

Figure 7:
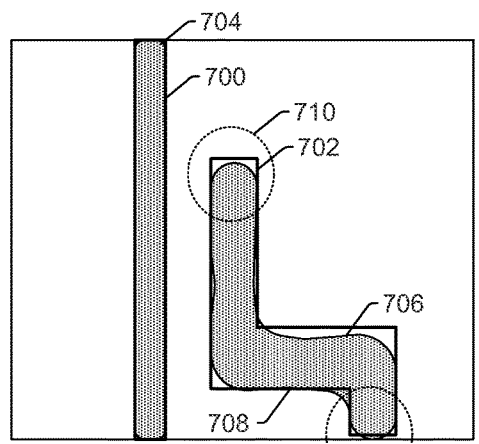
FIGS. 7-8 are schematic diagrams illustrating plan views of different examples of results of currently used methods for aligning a portion of a design for a wafer in design space with the portion of the design for the wafer in wafer space.
Figure 8:
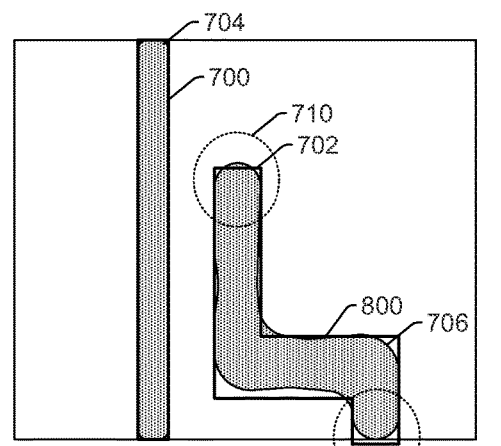

In some embodiments of aligning the output of the measurement subsystem to the design, imaginary center lines drawn through the patterned features in the output and the design may be used for fine alignment (whereas the alignment marks described further herein may be used for global alignment of a wafer or one or more FOVs). FIGS. 7 and 8 illustrate some issues that can arise when using edges of features in the output and the design for alignment. For example, as shown in FIG. 7, a portion of a design may include two features, line 700 and polygon 702. In addition, a portion of output generated by the measurement subsystem corresponding to the portion of the design may include output for two features, line 704 and polygon 706. The features in the design and the output of the measurement subsystem appear differently due to the printing of the design on the wafer as described further above.

Output of the measurement subsystem (e.g., a SEM image) can be aligned to a design using edge-to-edge approaches at the upper edge or lower edge of a pattern of interest. For example, as shown in FIG. 7, if lower edges 708 of the horizontal portions of polygons 702 and 706 are used for alignment, then the line end measurements performed for polygon 706 in areas 710 and 712 of the polygon will produce one measurement. However, if, as shown in FIG. 8, upper edges 800 of the horizontal portions of polygons 702 and 706 are used for alignment, then the line end measurements performed for polygon 706 in areas 710 and 712 of the polygon will produce a different measurement. In this manner, depending on which edge of the polygon is used for alignment of the design to the output, the line end measurements will produce different results, which is disadvantageous for a number of obvious reasons (e.g., the line end pull back measurements are inconsistent).

Figure 9:
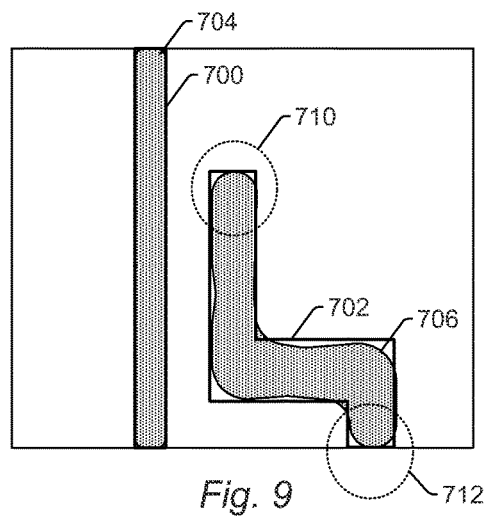
FIG. 9 is a schematic diagram illustrating a plan view of one example of results of an embodiment for aligning a portion of a design for a wafer in design space with the portion of the design for the wafer in wafer space.

Instead of using edge-to-edge alignment, therefore, the embodiments described herein may perform alignment of measurement subsystem output to design using the centers of the features in the output and in the design. For example, as shown in FIG. 9, if the centers of polygons 702 and 706 are used for alignment, a different measurement will be produced for line end measurements performed for polygon 706 in areas 710 and 712 of the polygon than if either of the edge alignment methods described above are used. However, aligning the output of the measurement subsystem and the design using the centers of the features will produce a much more consistent alignment from ROI to ROI thereby providing substantially consistent measurements (e.g., corner measurements, line end pullback measurements, and width measurements) for ROIs. Using the centers of features for alignment rather than their edges can also improve the robustness of the alignment for severely distorted patterns and when the FOV does not have many features for aligning the patterns of interest.

Figures 10, 11:
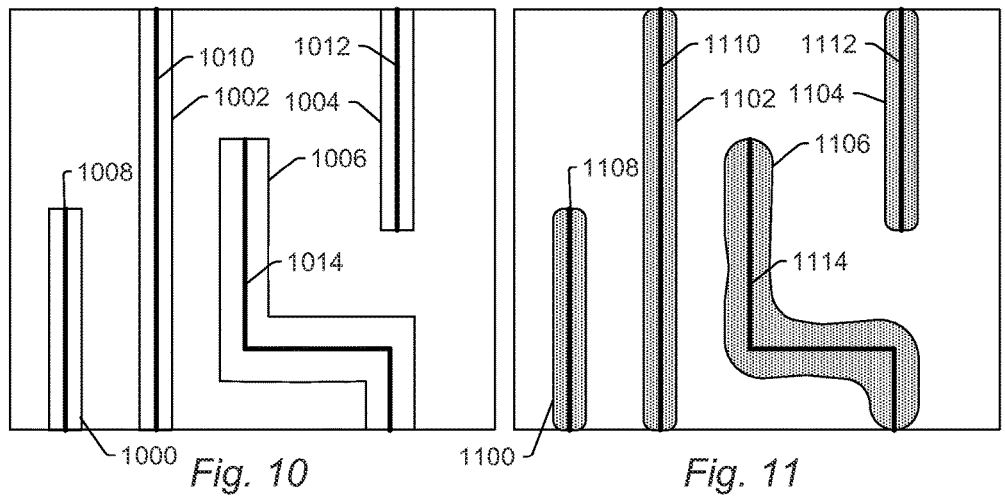
FIGS. 10-12 are schematic diagrams illustrating plan views of a portion of a design for a wafer in design and wafer space and how they can be aligned by embodiments described herein.
Figure 12:
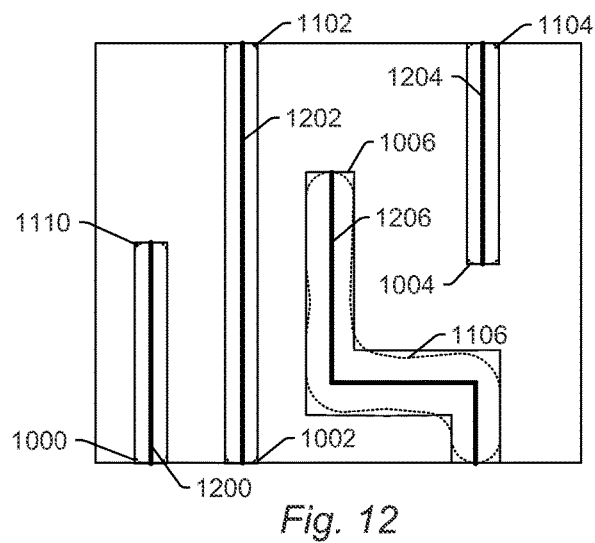

FIGS. 10-12 illustrate how the centers of patterned features in a portion of a design and in measurement subsystem output can be used for aligning the design to the output. For example, as shown in FIG. 10, a portion of a design for a specimen may include four different features, portions of lines 1000, 1002, and 1004 and polygon 1006. As further shown in FIG. 10, an imaginary center line can be determined through the entirety of the portion of each feature included in the portion of the design. For example, imaginary center lines 1008, 1010, and 1012 may be determined for portions of lines 1000, 1002, and 1004. In addition, imaginary center line 1014 may be determined for polygon 1006. The imaginary center lines may be determined in any suitable manner.

Imaginary center lines may also be determined for the patterned features as they appear in the measurement subsystem output. For example, as shown in FIG. 11, a portion of a design in measurement subsystem output may include four different features corresponding to those shown in FIG.

10, e.g., portions of lines 1100, 1102, and 1104 and polygon 1106. As further shown in FIG. 11, an imaginary center line can be determined through the entirety of the portion of each feature included in this portion of the design. For example, imaginary center lines 1108, 1110, and 1112 may be determined for portions of lines 1100, 1102, and 1104. In addition, imaginary center line 1114 may be determined for polygon 1106. The imaginary center lines may be determined as described further herein.

Since the center lines of the patterned features in the design can be determined reproducibly and since the center lines of the patterned features in the output should be able to be determined substantially reproducibly, the imaginary center lines can be used to align the patterned features in the design to the patterned features in the output relatively reproducibly. For example, as shown in FIG. 12, alignment 1200 of the center lines 1008 and 1108 can be used to reproducibly align line 1000 in the design to line 1100 in the output. In another example, alignment 1202 of the center lines 1010 and 1110 can be used to reproducibly align line 1002 in the design to line 1102 in the output. In addition, alignment 1204 of the center lines 1012 and 1112 can be used to reproducibly align line 1004 in the design to line 1104 in the output. Furthermore, alignment 1206 of the center lines 1014 and 1114 can be used to reproducibly align polygon 1006 in the design to polygon 1106 in the output.

Of course, to align the features in a portion of the design to the features in the same portion of the design in output of the measurement subsystem, not all of the center lines of all of the features in the portion have to be aligned to each other in order to produce alignment of all of the features to each other. For example, in the example shown in FIG. 12, alignment of the center lines of the polygon in the design and in the output may be used to produce fine design-to-output alignment for the polygon as well as the remaining features in this portion of the design. Reproducibly being able to align the features in the design to the features in the measurement subsystem output will improve the consistency of the measurements performed using the results of the alignment.

In a further embodiment, the parameter(s) of the measurement(s) include boundaries of one or more dimensions across which the measurement(s) are performed. For example, the computer subsystem(s) may be configured for automatic generation of measurement bounds. The measurement bounds may be automatically determined at runtime (no parameter needed during setup) for each unique site.

Figure 13:
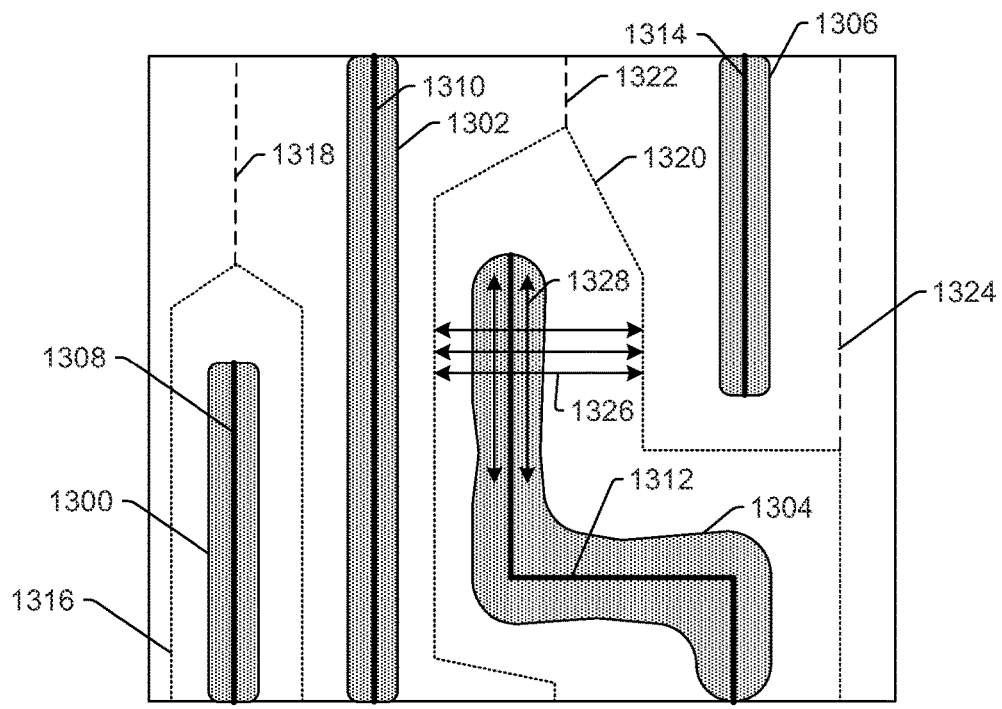
FIG. 13 is a schematic diagram illustrating a plan view of a portion of a design for a wafer in wafer space and how the dimensions across which a measurement may be performed can be determined by embodiments described herein.

In some embodiments, the boundaries of the dimensions across which the measurements are performed may be determined using the center lines described further herein. For example, as shown in FIG. 13, a portion of a design formed on a wafer may include four patterned features 1300, 1302, 1304, and 1306, which are shown in FIG. 13 as they might be formed on the wafer and then imaged by the measurement subsystem. Imaginary center lines 1308, 1310, 1312, and 1314 may be generated for each of the features as described further herein. Imaginary center lines may also be generated for the spaces between the patterned features. The center lines for the spaces may be defined by the midpoints between two adjacent features in the design. For example, center line 1316 may be defined based on the midpoints between the center lines of feature 1300 and any other adjacent features (e.g., feature 1302). Center line 1318 may be defined based on the midpoints between the center lines of feature 1302 and any other adjacent features on the left side of this feature (not shown in FIG. 13) and extending above feature 1300. Center line 1320 may be defined based on the midpoints between the center lines of feature 1304 and any other adjacent features (e.g., features 1302 and 1306). Center line 1322 may be defined based on the midpoints between the center lines of features 1302 and 1306. In addition, center line 1324 may be defined based on the midpoints between the center lines of feature 1306 and any adjacent features on the right side of this feature (not shown in FIG. 13). Although the center lines shown in FIG. 13 are described as being defined with respect to the patterned features as they appear in measurement subsystem output, the center lines may also or alternatively be defined based on the patterned features as they appear in the design itself. In addition, although the center lines in the spaces between the patterned features are described above as being defined based on the center lines in the patterned features, the center lines in the spaces may be defined based on some other characteristic of the patterned features (e.g., the edges of the patterned features).

The center lines in the spaces between the patterned features may then be used as the boundaries for any measurements of the patterned features that are performed. For example, as shown in FIG. 13, if a critical dimension (CD) of patterned feature 1304 is to be measured for this patterned feature, the measurement may be performed along one of lines 1326 from the location of center line 1320 on one side of the patterned feature to the location of center line 1320 on the other side of the patterned feature and in a direction that is substantially perpendicular to center line 1312 within patterned feature 1304. In this manner, the measurements may be performed in a direction that is orthogonal to the center lines through the patterned features. Although three lines 1326 are shown in FIG. 13 representing the dimensions across which different measurements may be performed for patterned feature 1304, any suitable number of such measurements may be performed at any suitable location along the center line within the patterned feature. In addition, the measurements may be performed in a direction substantially parallel to the center lines of the features. For example, as shown in FIG. 13, measurements may be performed along one of lines 1328 and, although not shown in FIG. 13, the boundaries of such measurements may also be determined by the center lines in the spaces between the patterned features as described further herein. Furthermore, although not shown in FIG. 13, the dimensions across which the measurements are performed may intersect the center lines of the patterned features and/or of the spaces between the patterned features at some angle other than orthogonal (e.g., for measuring radius, for line end pullback measurements, for line end distance measurements, etc.).

Using the center lines in the spaces between the patterned features as the boundaries for any measurements performed on the patterned features may advantageously ensure that the measurements begin and end outside of the patterned features thereby ensuring that the measurements are performed across an entire dimension of the patterned features and that the boundaries of the measurements are sufficiently outside of the patterned features such that the edges of the patterned features can be determined in the output generated during the measurements with sufficient accuracy and/or confidence. For instance, if the boundary at which a measurement begins is too close to the edge of a patterned feature, the location of the edge of the patterned feature within the output may be easily confused with the measurement boundary and/or may be missed in measurement boundary noise. However, using the center lines in the spaces between the patterned features to determine the boundaries of the measurements as described herein will substantially eliminate any such errors in patterned feature edge detection.

In a similar manner, if the measurements described herein are to be performed for a space between two patterned features (e.g., to measure the gap between two features), the boundaries for that measurement may be determined based on the center lines within the patterned features surrounding the space. In this manner, the measurement can begin and end at locations sufficiently beyond the edges of the space thereby ensuring that the measurement is performed across an entire dimension of the space and that the edges of the space can be determined with relatively high accuracy and/or confidence.

In one embodiment, the measurement(s) include automatically determining locations in the output generated by the detector during the measurement(s) of one or more edges of one or more structures formed on the specimen. In this manner, the embodiments described herein may be configured for automatic determination of SEM edge locations. In some instances, the edge locations may be determined using the 1D gradient profiles described further herein. For example, edge locations may be automatically determined by finding the strongest positive or negative gradient peaks within a 1D gradient profile. In other words, the peak points in the 1D gradient profile can be selected as the edge locations. A CD or other attributes of the features can then be determined based on the edge locations. For example, the top, middle, or bottom CD can be determined by locating the top, middle, or bottom edge locations using positive/negative gradient peaks, zero crossing or negative/positive gradient peaks of 1D gradient profiles orthogonal to a line drawn through the center of the structure. However, the edges can be located using other measurement algorithms besides using gradient profiles.

In another embodiment, the computer subsystem(s) are configured for automatically generating one or more attributes for one of the first and second subsets of the ROIs based on results of the measurement(s). In this manner, the embodiments described herein may be configured for automatic generation of measurement statistics and attributes for each ROI. The measurement statistics for each ROI may be determined independently from the metrology results for every other ROI. Various measurement statistics (e.g., Max, Min, Mean, Average, Median, Standard Deviation, Range, and Sum) may be generated using multiple measurements with a ROI. In another example, the computer subsystem(s) may be configured for automatic generation of other attributes such as one-dimensional (1D) gray scale profiles of a patterned structure formed on a wafer. The 1D gray scale profiles may be automatically generated by output generated along a line that is either orthogonal to a center line through the patterned structure or parallel to the center line through the patterned structure. The computer subsystem(s) may also be configured for automatic generation of 1D gradient profiles, which may be automatically generated by taking a gradient of a 1D gray scale profile determined as described above. In some instances, the multiple measurements within a ROI may include one measurement per 1D gray scale or gradient profile. The measurement statistics may be related to actual CD, positive delta CD, and negative delta CD, where the delta CD provides CD measurement relative to the design. In addition, various types of gray scale or gradient-based attributes (such as peak local gray level difference, peak positive or negative gradient, etc.) using 1D grayscale profiles parallel or orthogonal to a center line through a structure can be determined. The measurement statistics and/or attributes that can be determined using the embodiments described herein are also not limited to the ones described herein.

In an additional embodiment, the one or more computer subsystems are configured for automatically generating one or more attributes for multiple instances of the ROIs in one of the first and second subsets based on results of the one or more measurements and comparing at least one of the one or more attributes for two or more of the multiple instances to identify outliers in the two or more of the multiple instances. In this manner, the embodiments described herein may be configured for relative comparison of measurement statistics and attributes across various sites on a wafer to determine outliers. Measurement statistics and attributes for each of the ROIs can be compared across various sites on a wafer to determine outliers for defect detection.

In a further embodiment, the one or more computer subsystems are configured for automatically selecting one or more alignment sites in the design, and the metrology process includes determining one or more locations of at least one of the one or more alignment sites on the specimen during the metrology process and determining one or more locations of one or more of the ROIs in the first and second subsets on the specimen based on the one or more locations of the at least one alignment site on the specimen. For example, the embodiments described herein may be configured for generating alignment sites (for coarse alignment) automatically with physical design analysis. In one such example, during metrology plan generation, for each FOV, the computer subsystem(s) may be configured to automatically determine unique alignment site(s) and autofocus site(s) for each measurement site using the physical design. Automatically determining the unique alignment site(s) and autofocus site(s) may be performed using design analysis algorithms and software.

In some embodiments, the systems described herein may be configured to execute the metrology plan per FOV on a metrology tool that includes the measurement subsystem and at least one of the computer subsystems. In one such embodiment, the system may perform auto-focus per FOV and then anchor point alignment per FOV. In some such instances, the system may fetch design clips for the anchor point and measurement sites from a design database to be used for auto-focus and/or anchor point alignment. The system may further be configured for measurement site alignment per FOV and execute the metrology plan for the measurement site such as performing the selected types of measurements in ROI(s) within the FOV. The computer subsystem(s) may then produce measurement data per ROI.

In some embodiments, the metrology process includes determining if a defect is present in one of the ROIs in the first and second subsets based on only the one or more measurements performed in the one ROI. In other words, the defect detection in an ROI may not be based on the output generated in any other ROI (in the same die as the ROI or in a different die than the one in which the ROI is located) or any measurements produced using such output. For example, a measurement result generated for an ROI using only the output generated in that ROI may be compared to a threshold and any measurement result above the threshold may be determined to be a defect while any measurement result below the threshold may be determined to not be a defect (or vice versa). In addition, such defect detection may be performed using more than one threshold (e.g., upper and lower thresholds) and/or any other suitable defect detection method and/or algorithm.

In this manner, the metrology process for which the one or more parameters are determined may include ROI-based single die defect detection. Such defect detection may be performed to detect various defect types (e.g., pattern defects, missing and/or under-filled epitaxial layer, silicon germanium (SiGe) defects, etc.) by generating various types of attributes at the ROI locations (e.g., CD measurements, gradient magnitude, local gray level contrast, etc.).

In contrast to the embodiments described herein, currently used methods for ROI-based single die defect detection use a reference image or reference contours (acquired or generated) for defect detection. The acquired image approach has half the throughput as compared to ROI-based single die defect detection. The generated image or contour approach suffers from complexity and inaccuracies of generating the reference.

In one embodiment, the one or more measurements performed in one of the first and second subsets of the ROIs include CD measurements of one of the ROIs relative to CD measurements of others of the ROIs. In this manner, the measurements for which the one or more parameters are determined may be relative CD measurements in which the CD of multiple instances of a given pattern of interest (POI) on a given wafer may be compared. In other words, the CD measurements may be a relative measurement rather than an absolute measurement. In contrast to the embodiments described herein, currently used methods for relative CD measurement use a CD-SEM tool where recipe setup to define multiple ROIs per site is a very manual and time consuming process and so a substantially limited number of ROIs per site and a limited number of unique sites per die can be measured for the CD measurements.

In an additional embodiment, the one or more measurements performed in one of the first and second subsets of the ROIs include overlay measurements of one of the ROIs relative to overlay measurements of others of the ROIs. In this manner, the measurements for which the one or more parameters are determined may be relative overlay measurements. In other words, the overlay measurements may be a relative measurement rather than an absolute measurement. The overlay errors may be measured during multi-patterning fabrication processes (e.g., double, triple, or quad patterning), spacer pitch splitting fabrication processes, etc. In addition, the overlay errors may be measured between a current layer formed on the wafer and a previous layer formed on the wafer. In contrast to the embodiments described herein, currently used methods for relative overlay measurement use a CD-SEM tool where recipe setup to define multiple ROIs per site is a very manual and time consuming process and so a substantially limited number of ROIs per site and a limited number of unique sites per die can be measured for the overlay measurements.

In some embodiments, the specimen includes a process window qualification (PWQ) wafer, and the automatically generating includes automatically generating the ROIs to be measured during the metrology process based on the design and results of an inspection process performed on the specimen. In this manner, the measurements for which the one or more parameters are determined may include automated review of pattern defects on PWQ wafers (e.g., using CD measurements), which may be detected by a PWQ inspection of the wafer performed by an inspection tool such as one of the inspection tools commercially available from KLA-Tencor. In some instances, the defects detected by PWQ inspection may be used as hot spots for metrology, and measurements and detection performed at the metrology hot spots may be used for refining the PWQ window (e.g., the window of process parameters for which PWQ is performed). Currently used methods for automated PWQ review of pattern defects perform manual or automated design-based review of pattern defects found by a PWQ inspection. The manual method is inaccurate and unreliable (e.g., a user can miss complete pattern failures or can be unable to distinguish substantially subtle (e.g., 3 to 7 nm) CD variation) and the design-based approach requires recipe setup between the discovery and metrology steps.

PWQ inspection may be performed as described in U.S. Pat. No. 6,902,855 to Peterson et al. issued on Jun. 7, 2005, U.S. Pat. No. 7,418,124 to Peterson et al. issued on Aug. 26, 2008, U.S. Pat. No. 7,769,225 to Kekare et al. issued on Aug. 3, 2010, U.S. Pat. No. 8,041,106 to Pak et al. issued on Oct. 18, 2011, and U.S. Pat. No. 8,213,704 to Peterson et al. issued on Jul. 3, 2012, which are incorporated by reference as if fully set forth herein. The embodiments described herein may include any step(s) of any method(s) described in these patents and may be further configured as described in these patents. A PWQ wafer may be printed as described in these patents.

In a further embodiment, the metrology process is performed on the specimen during inline monitoring of a fabrication process performed on the specimen. In this manner, the metrology process for which one or more parameters are determined may include a metrology process that is performed during inline monitoring (i.e., measurements performed on a wafer produced by a production fabrication process). Such metrology processes may be performed for measurements such as gate critical dimension uniformity (CDU) measurements, line edge roughness (LER)/line width roughness (LWR) measurements, CD/overlay measurements, etc.

In another embodiment, the automatically generating includes automatically generating the ROIs to be measured during the metrology process based on the design and results of an inspection process performed on the specimen. For example, inline monitoring may also be performed for locations of defects detected by inspection such that the locations of the detected defects are used essentially as "hot spots" for inspection guided metrology. In some such embodiments, the results of metrology may be correlated to the results of inspection. For example, in some instances, a pattern fidelity signature generated by inspection may be correlated to measurements performed during metrology.

In contrast to the embodiments described herein, the currently used methods for metrology during inline monitoring use a CD-SEM tool to perform CD/overlay measurements at specific metrology targets (e.g., printed in the scribe lines on the wafer) and since the recipe setup is quite manual in defining ROIs, it is not able to automatically measure thousands of unique sites on a wafer. Some other currently used methods for inline monitoring include using a SEM review tool to randomly sample a few locations from millions of hot spot locations to perform critical point inspection (CPI) using a die-to-die mode. However, since the hot spot locations are sampled randomly, the currently used methods can miss a substantially large number of hot spot defects.

In an additional embodiment, the one or more computer subsystems are configured for comparing the one or more measurements performed in one of the first and second subsets of the ROIs to design intent for the one of the first and second subsets of the ROIs and modifying an optical proximity correction (OPC) model based on results of the comparing. In this manner, the metrology process for which the one or more parameters are determined may be performed for OPC model verification against design intent. In contrast to the embodiments described herein, currently used methods for OPC model verification against design intent use a CD-SEM tool where recipe setup to define multiple ROIs per site is a very manual and time consuming process and so very limited number of ROIs per site and limited number of unique sites per die can be measured for CD measurements. For OPC, it is required to automatically discover weak structures and immediately and/or automatically setup and measure thousands of unique sites per die.

In another embodiment, the one or more computer subsystems are configured for detecting defects in one of the first and second subsets of the ROIs based on the one or more measurements and reporting the one or more measurements as defect attributes for the detected defects. In this manner, the metrology process may include reporting pattern fidelity measurements as defect attributes at the defect locations reported by a redetection algorithm. In contrast to the embodiments described herein, currently used methods do not report measurement statistics as part of defect attributes and so cannot quantify whether a pattern distortion is a nuisance, partial break, full break, partial bridge, or full bridge.

The embodiments described herein have a number of advantages over currently used methods for determining one or more parameters for a metrology process. For example, the embodiments described herein provide a substantially fast automated on-the-fly mechanism to generate ROIs for thousands of unique sites and then automatically generate various measurement statistics and attributes for each ROI across various sites (using SEM image and physical design clip for a given site), which could then be used to serve various use cases described herein.

Another embodiment relates to a computer-implemented method for determining one or more parameters of a metrology process to be performed on a specimen. The method includes the automatically generating and automatically determining steps described above.

Each of the steps of the method may be performed as described further herein. The method may also include any other step(s) that can be performed by the measurement subsystem and/or computer subsystem(s) or system(s) described herein. The automatically generating and automatically determining steps are performed by one or more computer systems, which may be configured according to any of the embodiments described herein. In addition, the method described above may be performed by any of the system embodiments described herein.

Figure 14:
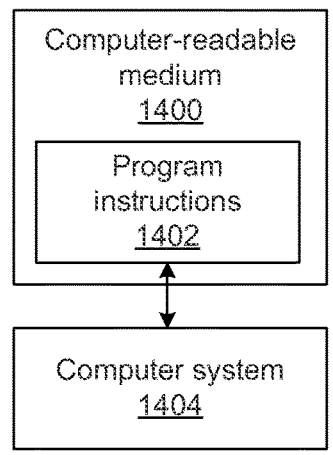
FIG. 14 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on a computer system for performing a computer-implemented method for determining one or more parameters of a metrology process to be performed on a specimen. One such embodiment is shown in FIG. 14. In particular, as shown in FIG. 14, non-transitory computer-readable medium 1400 includes program instructions 1402 executable on computer system 1404. The computer-implemented method may include any step(s) of any method(s) described herein.

Program instructions 1402 implementing methods such as those described herein may be stored on computer-readable medium 1400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 1404 may be configured according to any of the embodiments described herein.

Further modifications and alternative embodiments of various aspects of the invention will be apparent to those skilled in the art in view of this description. For example, methods and systems for determining one or more parameters of a metrology process to be performed on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine one or more parameters of a metrology process to be performed on a specimen, comprising:
    a measurement subsystem comprising at least an energy source and a detector, wherein the energy source is configured to generate energy that is directed to a specimen, and wherein the detector is configured to detect energy from the specimen and to generate output responsive to the detected energy; and
    one or more computer subsystems configured for:
        automatically generating regions of interest to be measured during a metrology process performed for the specimen with the measurement subsystem based on a design for the specimen; and
        automatically determining one or more parameters of one or more measurements performed in first and second subsets of the regions of interest during the metrology process with the measurement subsystem based on portions of the design for the specimen located in the first and second subsets of the regions of interest, respectively, wherein the one or more parameters of the one or more measurements performed in the first subset are determined separately and independently of the one or more parameters of the one or more measurements performed in the second subset, and wherein the design for the specimen used for said automatically generating and said automatically determining does not include features of the design that will not be printed on the specimen.

2. The system of claim 1, wherein said automatically generating and said automatically determining are performed during setup of the metrology process.

3. The system of claim 1, wherein said automatically generating and said automatically determining are performed on-the-fly during runtime of the metrology process.

4. The system of claim 1, wherein said automatically generating comprises performing rules-based searching of the design during setup of the metrology process.

5. The system of claim 1, wherein the one or more computer subsystems comprise a computer subsystem of an electronic design automation tool.

6. The system of claim 1, wherein the one or more parameters automatically determined for the first subset of the regions of interest result in a first type of the one or more measurements performed in the first subset of the regions of interest, wherein the one or more parameters automatically determined for the second subset of the regions of interest result in a second type of the one or more measurements performed in the second subset of the regions of interest, and wherein the first and second types of the one or more measurements are different from each other.

7. The system of claim 1, wherein the one or more computer subsystems are further configured for determining locations on the specimen of the first and second subsets of the regions of interest during the metrology process by aligning the output of the detector to the design for the specimen.

8. The system of claim 1, wherein the one or more parameters of the one or more measurements comprise boundaries of one or more dimensions across which the one or more measurements are performed.

9. The system of claim 1, wherein the one or more measurements comprise automatically determining locations in the output generated by the detector during the one or more measurements of one or more edges of one or more structures formed on the specimen.

10. The system of claim 1, wherein the one or more computer subsystems are further configured for automatically generating one or more attributes for one of the first and second subsets of the regions of interest based on results of the one or more measurements.

11. The system of claim 1, wherein the one or more computer subsystems are further configured for automatically generating one or more attributes for multiple instances of the regions of interest in one of the first and second subsets based on results of the one or more measurements and comparing at least one of the one or more attributes for two or more of the multiple instances to identify outliers in the two or more of the multiple instances.

12. The system of claim 1, wherein the one or more computer subsystems are further configured for automatically selecting one or more alignment sites in the design, and wherein the metrology process comprises determining one or more locations of at least one of the one or more alignment sites on the specimen during the metrology process and determining one or more locations of one or more of the regions of interest in the first and second subsets on the specimen based on the one or more locations of the at least one alignment site on the specimen.

13. The system of claim 1, wherein the metrology process comprises determining if a defect is present in one of the regions of interest in the first and second subsets based on only the one or more measurements performed in the one region of interest.

14. The system of claim 1, wherein said automatically generating comprises automatically generating the regions of interest to be measured during the metrology process based on the design and results of an inspection process performed on the specimen.

15. The system of claim 1, wherein the one or more measurements performed in one of the first and second subsets of the regions of interest comprise critical dimension measurements of one of the regions of interest relative to critical dimension measurements of others of the regions of interest.

16. The system of claim 1, wherein the one or more measurements performed in one of the first and second subsets of the regions of interest comprise overlay measurements of one of the regions of interest relative to overlay measurements of others of the regions of interest.

17. The system of claim 1, wherein the specimen comprises a process window qualification wafer, and wherein said automatically generating comprises automatically generating the regions of interest to be measured during the metrology process based on the design and results of an inspection process performed on the specimen.

18. The system of claim 1, wherein the metrology process is performed on the specimen during inline monitoring of a fabrication process performed on the specimen.

19. The system of claim 1, wherein the one or more computer subsystems are further configured for comparing the one or more measurements performed in one of the first and second subsets of the regions of interest to design intent for the one of the first and second subsets of the regions of interest and modifying an optical proximity correction model based on results of said comparing.

20. The system of claim 1, wherein the one or more computer subsystems are further configured for detecting defects in one of the first and second subsets of the regions of interest based on the one or more measurements and reporting the one or more measurements as defect attributes for the detected defects.

21. The system of claim 1, wherein the specimen comprises a wafer.

22. The system of claim 1, wherein the specimen comprises a reticle.

23. The system of claim 1, wherein the energy directed to the specimen comprises light, and wherein the energy detected from the specimen comprises light.

24. The system of claim 1, wherein the energy directed to the specimen comprises electrons, and wherein the energy detected from the specimen comprises electrons.

25. The system of claim 1, wherein the energy directed to the specimen comprises ions.

26. A non-transitory computer-readable medium, storing program instructions executable on a computer system for performing a computer-implemented method for determining one or more parameters of a metrology process to be performed on a specimen, wherein the computer-implemented method comprises:

automatically generating regions of interest to be measured during a metrology process performed for a specimen with a measurement subsystem based on a design for the specimen, wherein the measurement subsystem comprises at least an energy source and a detector, wherein the energy source is configured to generate energy that is directed to the specimen, and wherein the detector is configured to detect energy from the specimen and to generate output responsive to the detected energy; and automatically determining one or more parameters of one or more measurements performed in first and second subsets of the regions of interest during the metrology process with the measurement subsystem based on portions of the design for the specimen located in the first and second subsets of the regions of interest, respectively, wherein the one or more parameters of the one or more measurements performed in the first subset are determined separately and independently of the one or more parameters of the one or more measurements performed in the second subset, and wherein the design for the specimen used for said automatically generating and said automatically determining does not include features of the design that will not be printed on the specimen.

27. A computer-implemented method for determining one or more parameters of a metrology process to be performed on a specimen, comprising:

automatically generating regions of interest to be measured during a metrology process performed for a specimen with a measurement subsystem based on a design for the specimen, wherein the measurement subsystem comprises at least an energy source and a detector, wherein the energy source is configured to generate energy that is directed to the specimen, and wherein the detector is configured to detect energy from the specimen and to generate output responsive to the detected energy; and automatically determining one or more parameters of one or more measurements performed in first and second subsets of the regions of interest during the metrology process with the measurement subsystem based on portions of the design for the specimen located in the first and second subsets of the regions of interest, respectively, wherein the one or more parameters of the one or more measurements performed in the first subset are determined separately and independently of the one or more parameters of the one or more measurements performed in the second subset, wherein the design for the specimen used for said automatically generating and said automatically determining does not include features of the design that will not be printed on the specimen, and wherein said automatically generating and said automatically determining are performed by one or more computer systems.

* * * * *